United States Patent [19]

Swoboda

[11] 4,442,700

[45] Apr. 17, 1984

[54] ULTRASONIC HYDROMETER

[75] Inventor: Carl A. Swoboda, Naperville, Ill.

[73] Assignee: The United States of America as represented by the United States Department of Energy, Washington, D.C.

[21] Appl. No.: 356,567

[22] Filed: Mar. 9, 1982

[51] Int. Cl.³ ............................................... G01N 9/00
[52] U.S. Cl. ..................................... 73/32 A; 73/597
[58] Field of Search ....................... 73/597, 32 A, 32 R

[56] References Cited

U.S. PATENT DOCUMENTS

| 3,028,749 | 4/1962 | Welkowitz | 73/32 A |
| 3,648,513 | 3/1972 | Patterson | 73/597 X |
| 4,235,099 | 11/1980 | Ishizaka | 73/32 A |

FOREIGN PATENT DOCUMENTS

| 52-11090 | 1/1977 | Japan | 73/32 A |
| 56-6133644 | 10/1981 | Japan | 73/32 A |

OTHER PUBLICATIONS

"Sound Velocimeters Monitor Process Streams" by Zacharias et al., from Chemical Engineering Jan. 22, 1973.

Primary Examiner—James J. Gill
Attorney, Agent, or Firm—Hugh W. Glenn; Charles F. Lind; Michael F. Esposito

[57] ABSTRACT

The disclosed ultrasonic hydrometer determines the specific gravity (density) of the electrolyte of a wet battery, such as a lead-acid battery. The hydrometer utilizes a transducer that when excited emits an ultrasonic impulse that traverses through the electrolyte back and forth between spaced sonic surfaces. The transducer detects the returning impulse, and means measures the time "t" between the initial and returning impulses. Considering the distance "d" between the spaced sonic surfaces and the measured time "t", the sonic velocity "V" is calculated with the equation "$V=2d/t$". The hydrometer also utilizes a thermocouple to measure the electrolyte temperature. A hydrometer database correlates three variable parameters including sonic velocity in and temperature and specific gravity of the electrolyte, for temperature values between 0° and 40° C. and for specific gravity values between 1.05 and 1.30. Upon knowing two parameters (the calculated sonic velocity and the measured temperature), the third parameter (specific gravity) can be uniquely found in the database. The hydrometer utilizes a microprocessor for data storage and manipulation. The disclosed modified battery has a hollow spacer nub on the battery side wall, the sonic surfaces being on the inside of the nub and the electrolyte filling between the surfaces to the exclusion of intervening structure. An accessible pad exposed on the nub wall opposite one sonic surface allows the reliable placement thereagainst of the transducer.

6 Claims, 6 Drawing Figures

ULTRASONIC HYDROMETER

CONTRACTUAL ORIGIN OF THE INVENTION

The United States Government has rights in this invention pursuant to Contract No. W-31-109-ENG-38 between the U.S. Department of Energy and the University of Chicago representing Argonne National Laboratory.

BACKGROUND OF THE INVENTION

In a conventional lead-acid battery, a battery case defines interior cells, and spaced plates or electrodes are located within each cell submerged in a battery electrolyte. The lead-acid battery generally uses highly reactive sponge lead for the negative electrode, lead dioxide for the positive electrode, and a liquid solution of sulfuric acid for the electrolyte. The generalized equation for the electrochemical reaction within the cell when discharging and when being charged is:

$$PbO_2 + Pb + 2H_2SO_4 \underset{\text{CHARGE}}{\overset{\text{DISCHARGE}}{\rightleftarrows}} 2PbSO_4 + 2H_2O \quad \text{Eq. (1)}$$

This electrochemical reaction causes a measurable change in the specific gravity or density of the electrolyte. In determining the state-of-charge or operational readiness of a lead-acid battery, information regarding the specific gravity or density of the electrolyte in addition to voltage current, and temperature thus is desired. The specific gravity of the electrolyte in a lead-acid battery changes between a low value of 1.05–1.15 when the battery is in a discharged state and a high value of 1.25–1.35 when the battery is in a fully charged state.

Knowing this, it has been commonplace to measure with a hydrometer the specific gravity of the battery electrolyte to determine the vitality of the battery. To use the hydrometer, the battery filler cap must be removed in order to insert a hydrometer tube into the battery cell so as to draw the electrolyte into the hydrometer. The hydrometer has a float that bobs within the electrolyte to a specific depth, and this float is visually sighted against a scale to determine a specific gravity reading. For good accuracy, the reading must be adjusted for the difference between the electrolyte temperature and a normalized temperature, commonly considered to be 25° C., since the specific gravity varies substantially as a function of temperature.

Use of the hydrometer can be difficult and/or dangerous and/or tedious. For example, the battery can be located in a vehicle chassis where it could be difficult to obtain the electrolyte sample and/or have good sight of the positioned hydrometer. The battery electrolyte must be taken from the battery so that the possibility exists that it can be spilled onto the vehicle or onto the person, causing damage to either, or it can be contaminated before being put back into the battery. Moreover, as the float must be free to bob or move within the hydrometer, the hydrometer must be precisely oriented in a vertical manner when taking the reading. Once the electrolyte is discharged from the hydrometer back into the battery cell, the reading is lost and there is no permanent record. The required removal of the battery filler caps, etc. can be quite tedious if a large number of batteries must be charged and checked on a regular basis. Moreover, a true test would have to be made on all six battery cells; but this is not done as a matter of course and only a rough approximation of the battery condition is obtained by testing just one of the battery cells. Moreover, a maintenance-free battery does not even have a removable cap so that the float type hydrometer technique of testing the battery cannot even be used.

SUMMARY OF THE INVENTION

This invention relates to an improved design of a typical wet cell battery, such as a lead-acid battery, that allows the use of improved apparatus for and method of determining this condition of the battery by specifically measuring the speed or velocity of a pulsed sound wave through the liquid electrolyte and calibrating this against a database including a correction for temperature to find the specific gravity of the electrolyte.

This invention specifically provides, in one preferred embodiment, for determining the specific gravity of the electrolyte in the typical lead-acid battery without directly contacting the electrolyte. This allows the invention to be used both on batteries having removable water filler caps but without removing the caps and/or on maintanance-free batteries formed without removable filler caps.

The velocity of sound in a liquid is governed by the specific gravity or density and the compressibility of the liquid, and is given by the equation:

$$V = \sqrt{\frac{1}{\rho\beta}} \quad \text{Eq. (2)}$$

$V$ = Velocity
$\rho$ = Density
$\beta$ = Isothermal Compressibility

An alternative to the calculation form Eq. (2) involves the experimental generation of a database relating the specific gravity, temperature, and sonic velocity for appropriate concentration of the electrolyte, such as sulfuric acid, and using this database to find a missing value of any one of them when the other two are known. Thus, once a database is available, the specific gravity could be determined by knowing the sonic velocity and temperature of the electrolyte.

The properties of sound transmission are being used in many different applications, including level or flow detection of gases and liquids and nondestructive fault detection in solids. The basic theory utilizes the different transmission and reflection characteristics of the sonic wave at a boundary between dissimilar media. When a sound wave strikes the boundary between two different transmission media, part of the energy is reflected and part is transmitted. With a battery case of polypropylene having a sonic surface located below the level of the electrolyte, a pulse-echo technique would work by placing a transducer on the outside case of the battery. The sonic wave would be transmitted through the polypropylene to the electrolyte and would reflect off the opposite boundary, either a spaced second sonic surface or the surface of the electrolyte, to return back toward the first sonic surface to be detected then by the transducer receiver.

A specific object of this invention is to provide a battery design having spaced sonic surfaces inside the battery case that are constantly under the level of the battery electrolyte, where there is no intervening structure between these sonic surfaces to allow for the sonic pulse transmission back and forth between the surfaces. The spaced sonic surfaces can be spaced vertically, horizontally, or at an angle. Some existing batteries have pairs of spacer nubs formed on the exterior of the side walls for maintaining battery separation from adjacent structures for air cooling the battery. In one battery embodiment, it is contemplated that these spacer nubs can be enlarged, can be made hollow, and the spaced sonic surfaces could be formed at the opposite interior ends of the nubs.

The invention provides further an ultrasonic hydrometer apparatus having a probe that can be positioned against the outside of the battery case wall opposite one of the sonic surfaces. Upon being activated, the probe as positioned would transmit an ultrasonic impulse through the battery case wall and from the one surface through the battery electrolyte to reflect off the spaced boundary and/or sonic surface and travel again through the electrolyte to be detected by the same probe. The lapsed time for this impulse to travel back and forth between the spaced sonic surfaces would be measured, and the sonic velocity in the liquid would be determined.

To utilize the pulse-echo method, a 5 MHz transducer is used for both sending and receiving the signal. An initial pulse from a generator drives the transducer, and resets and starts a timer. The pulse propagates through the electrolyte and is reflected back and detected by the transducer. The received echo is conditioned and is used to stop the timer. The time measured is the time required for the pulse to travel twice the distance "d" between the spaced sonic surfaces. The velocity can be determined from this data by using the equation $$V=2d/t \qquad \text{Eq. (3)}$$

where
  d = distance between sonic surfaces;
  t = total pulse transit time.

One general object of this invention is to provide a portable ultrasonic hydrometer apparatus to allow an operator (tester) to go to and test a battery; and further whereupon a probe of the apparatus need only be applied against the exterior of the battery case without removing any battery caps or the like. A thermocouple further is located in the probe to measure the temperature of the battery electrolyte so that proper adjustments in the readings can be made to a reference temperature. A modified ultrasonic portable hydrometer apparatus is also disclosed which closely resembles a conventional battery testing hydrometer in that to use it some battery electrolyte is withdrawn from the battery to fill a closed ended housing having the spaced sonic surfaces and transducers; but the operation thereafter of these two embodiments would generally be similar.

It is contemplated that after obtaining the two inputs, namely the sonic velocity in and the temperature of the battery electrolyte, these inputs would be compared against an appropriate database so that a single specific gravity can be correlated to these paired inputs, to apprise of the corresponding relative condition of the battery.

The database disclosed herein has been obtained experimentally and correlates the sonic velocity of sulfuric acid for specific gravities in the range approximately between 1.05 and 1.30 for temperatures in the range between approximately 0°–40° C. Within these ranges, there is a unique or singular velocity at which sound will travel through the electrolyte for each paired combination of specific gravity and temperature. In other words, having a paired combination input for the sonic velocity and for the temperature, a singular specific gravity can be determined. However, beyond these ranges, it is possible to have dual values of specific gravity for a single input combination of sonic velocity and temperature. To eliminate this dual value phenomenon, the apparatus is constrained to operate only within these specific temperature and electrolyte concentration ranges; which is where the lead acid battery operates anyway. Of interest, at the specific gravity of approximately 1.24, the sonic velocity through the battery electrolyte is generally independent of temperature in this range and is approximately 1565 meters per second.

A specific microprocessor located in the ultrasonic hydrometer apparatus would have the necessary database and program for correlating lapsed time of the sonic impulses, and the temperature and the specific gravity of the electrolyte in question.

The invention allows the specific gravity of the battery electrolyte to be measured quickly and accurately—to the same, if not better degree of accuracy than that of a conventional float type hydrometer. Moreover, the ultrasonic hydrometer apparatus after once having been calibrated, could be operated by untrained personnel. There is no need for sight tubes and/or for maintaining a free floating bob, as in the hydrometer. With the basic invention, the measuring apparatus probe need not contact the battery electrolyte, and the specific gravity output could be given directly in digital format and retained until it is intentionally cancelled. Even the hydrometer type ultrasonic apparatus would have advantages over the conventional float hydrometer, since the tube need not be removed from the battery cell (less chances of spillage, damage or contamination) in order to obtain a reading, and the reading could be obtained almost instantaneously without the need for a specific vertical orientation of the apparatus.

DETAILED DESCRIPTION OF THE PREFERRED EMBODIMENT

Figure 1:
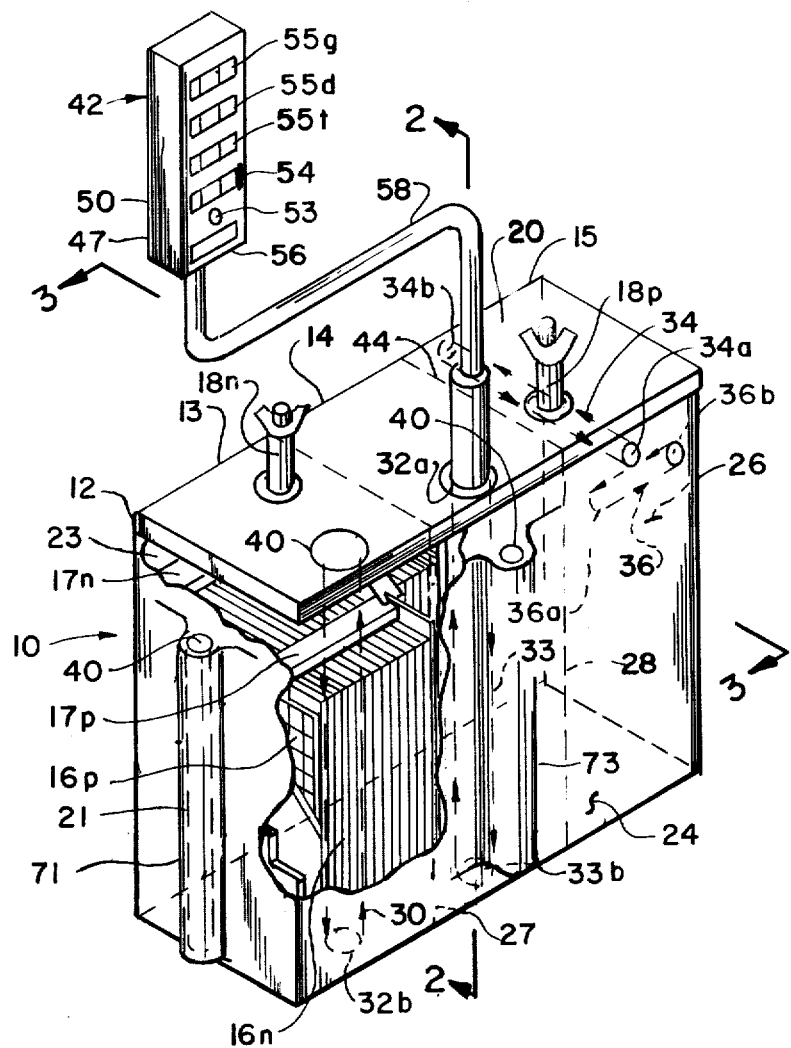
FIG. 1 is a perspective view of one embodiment of the subject ultrasonic hydrometer apparatus shown in operative association with a wet battery for determining the specific gravity of the battery electrolyte or liquid.

In FIG. 1, a battery 10 is illustrated having an exterior case 12 divided by separators into three cells 13, 14 and 15 as illustrated. Battery plates 16p and 16n are alternately spaced adjacent one another in each cell and a battery liquid or electrolyte fills each cell covering the plates. In the battery illustrated, the positive and negative plates 16p and 16n respectively, of the three cells 13, 14 and 15 would typically be connected together internally of the case by buss bars 17p and 17n and ultimately exposed at positive and negative terminals 18p and 18n, respectively. In a three-cell battery, the battery output between the terminals would be approximately 6 volts.

The case 12 is typically formed of polypropylene. This case construction is resistant against the electrolyte, further is liquid-tight to confine the electrolyte within each cell, and further effectively transmits ultrasonic impulses. The battery case 12 illustrated specifically has a top wall 20, a bottom wall 22, opposed pairs of side walls 23, 24 and 25 and 26, and the separator walls 27 and 28 located specifically between the battery cells.

Figure 2:
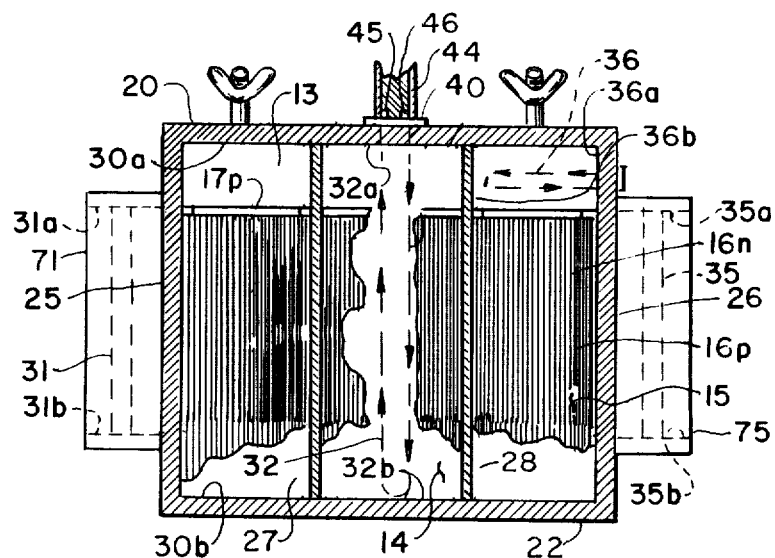
FIG. 2 is a sectional view as seen generally from line 2—2 in FIG. 1.
Figure 3:
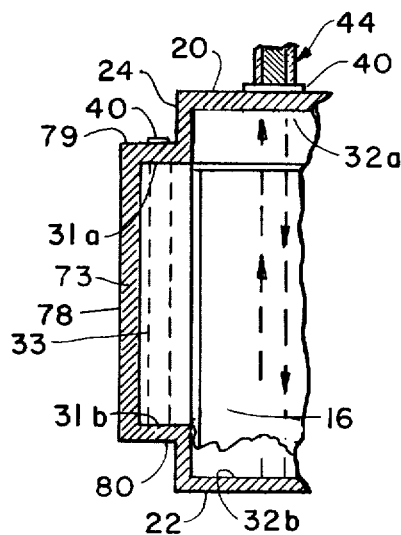
FIG. 3 is a sectional view as seen generally from line 3—3 in FIG. 1, illustrating a modification that can be made to a battery to make it particularly suited for allowing the use of the subject invention.

Opposing surfaces are formed on the battery case walls, under the level of the electrolyte, and can be used for practicing the particular invention. As illustrated in FIGS. 1, 2 and 3, in cell 13 there are opposed surfaces 30a and 30b that define therebetween a sonic path 30, and opposed surfaces 31a and 31b that define therebetween a sonic path 31; whereas cell 14 shows opposed surfaces 32a and 32b defining therebetween sonic path 32, and opposed surfaces 33a and 33b defining therebetween sonic path 33; while cell 15 shows three sets of opposed surfaces, surfaces 34a and 34b defining therebetween sonic path 34, surfaces 35a and 35b defining therebetween sonic path 35, and surfaces 36a and 36b defining sonic path 36.

Referring also now to FIGS. 2 and 3, the sonic path 32 extends between the opposing surfaces 32a and 32b formed on the top wall 20 and bottom wall 22, respectively, and there is no intervening structure therebetween, such as any of battery plates 16p and 16n, or wall structure. A pad area 40 is preferably defined on the exterior of top wall 20 proximate the sonic path 32, operable to highlight the location of the sonic path 32 and to allow for good sonic conductivity as will be noted.

Figure 5:
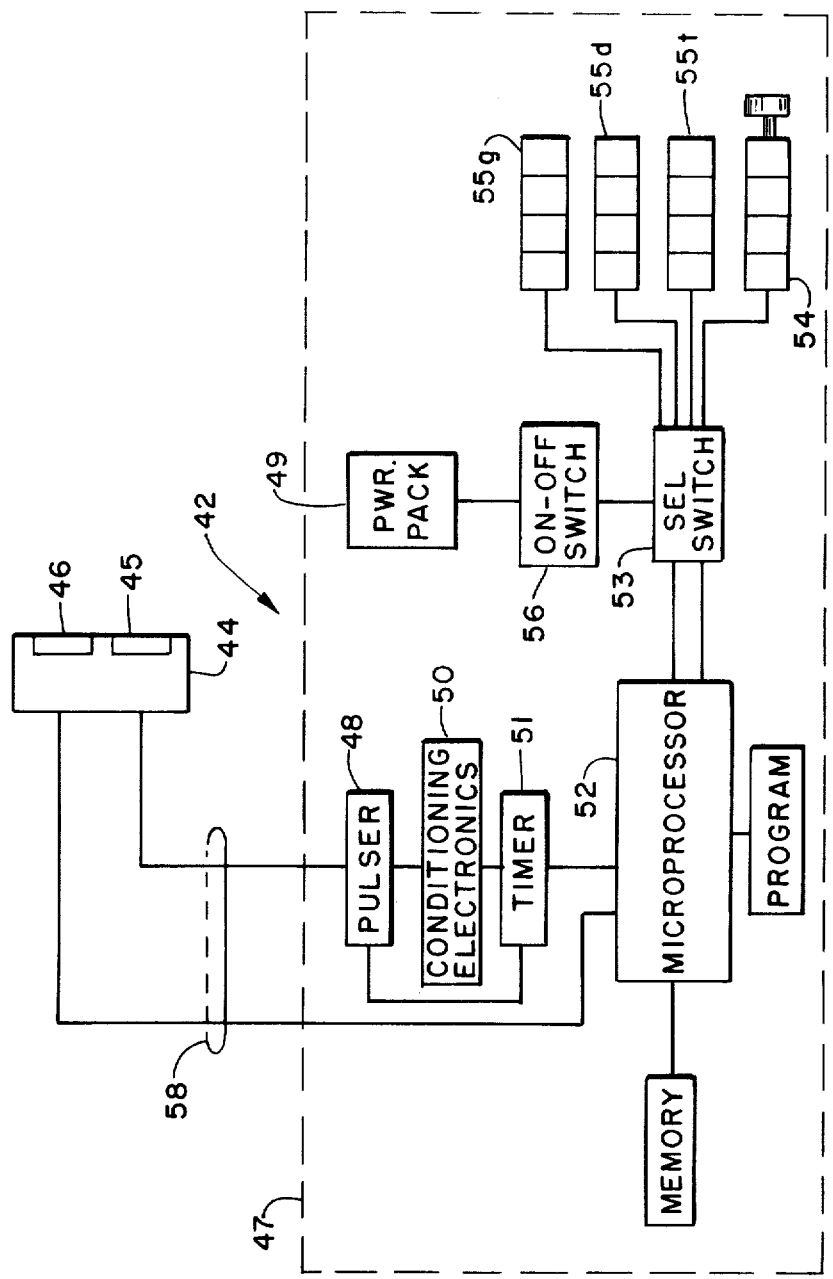
FIG. 5 is a schematic block diagram of the operative control used in the probe apparatus disclosed herein.

An ultrasonic hydrometer apparatus 42, illustrated in FIGS. 1, 2 and 5, includes a probe head 44 having therein a transducer 45 and a thermocouple 46. The apparatus further includes a housing 47 within which is located a pulser 48, battery or power source 49, conditioning electronics package 50, timer 51, and microprocessor 52 including a memory for a database and a control program. The apparatus further has in the housing 47 a mode selector switch 53, a thumb wheel switch 54, digital displays 55g, 55d, 55t for indicating the specific gravity, distance and temperature, and an on/off switch 56. A cable 58 having the appropriate connecting conductors therein extends between the housing 47 and the probe head 44.

As illustrated schematically in FIG. 5, the pulser 48 is connected to the transducer 45 and when energized would excite the transducer to emit then an ultrasonic signal. The transducer 45 would be mounted in the probe head 44 so that its output face could be pressed flush against the pad area 40 (see FIGS. 2 and 3) for transmitting this signal effectively to the battery case wall. The sound would be transmitted then through the battery case wall 20, and from sonic surface 32a through the battery electrolyte to reflect off the opposite sonic surface 32b and travel back through the electrolyte to be picked up by the transducer 45, now acting as a receiver. The pulser 48 also is connected to the timer 51 to start the timing cycle when the transducer is initially activated, and the transducer 45 is also connected through an electronic package 50 to the timer so that the returning signal detected by the transducer 45 is also impulsed to the timer to stop the timer. The electronics package 50 (not shown in detail) would include a blocking gate to preclude the initial transducer pulse from passing on to the timer stop control but which thereafter would open to allow the echo pulse through; filter and amplifier means to sort out and amplify the returning signals and a comparator to pass only the real impulse signal which will be much stronger than any secondary or background type return pulses the transducer will be receiving. The timer 51 thus measures the time it takes for the sonic impulse to travel through the electrolyte back and forth (or twice the distance between) the spaced sonic surfaces 32a and 32b, and this determination is passed on as an input to the microprocessor 52. The thermocouple 46 on the probe head 44 measures the battery case temperature, which under steady conditions would approximate the battery electrolyte temperature, and inputs this also to the microprocessor 52.

Thus, two inputs are obtained: the transit time "t" for the sonic pulse to travel twice the distance "d" between the spaced sonic surfaces 30a and 30b, and the temperature of the battery electrolyte. Knowing the distance "d" between the spaced surfaces 32a and 32b(or the surfaces of any of the other sonic paths), the sonic velocity can be directly determined by the equation $$V = 2d/t \qquad \text{Eq. (3)}$$

where
 V = sonic velocity in the electrolyte,
 d = distance between the sonic surfaces,
 t = total time between sending and receiving impulses.

Figure 6:
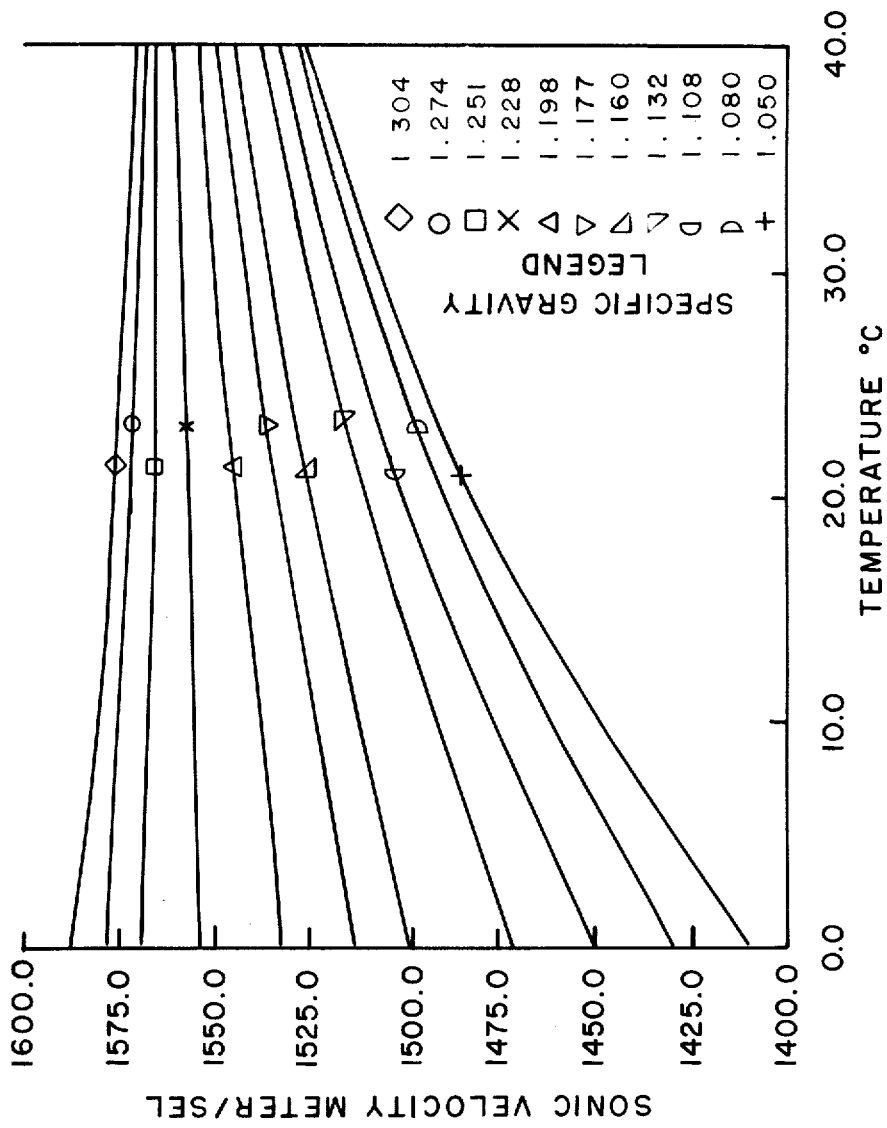
FIG. 6 is a graphic illustration of the database, used in the practice of the subject invention, correlating the sonic velocity in and specific gravity and temperature of the battery electrolyte.

The microprocessor 52 would thereupon process this calculation to obtain the sonic velocity through the electrolyte. The temperature of the electrolyte would be used as another input value. The microprocessor further would have in memory a database uniquely correlating the sonic velocity in the electrolyte at varying temperatures in the range between approximately 0° and 40° and at varying specific densities or gravities in the range between approximately 1.05 and 1.30 for the electrolyte of sulfuric acid ($H_2SO_4$). The graphic representation of this database is shown in FIG. 6, and specific values are arranged in matrix format in Table I. Having this database and two parameter inputs of the three interrelated parameters, the third parameter can be determined.

TABLE I

Database Values Correlating Sonic Velocity, Specific Gravity and Temperature in Electrolyte $H_2SO_4$

| TEMP (DEG C.) | \multicolumn{12}{c}{SPECIFIC GRAVITY} | | | | | | | | | | | |
|---|---|---|---|---|---|---|---|---|---|---|---|---|
| | 1.026 | 1.050 | 1.080 | 1.108 | 1.131 | 1.160 | 1.177 | 1.198 | 1.228 | 1.251 | 1.274 | 1.304 |
| 0 | 1403.167 | 1410.267 | 1429.753 | 1449.969 | 1471.640 | 1498.049 | 1513.135 | 1532.051 | 1551.864 | 1568.343 | 1577.938 | 1585.758 |
| 1 | 1407.052 | 1414.538 | 1432.480 | 1451.796 | 1473.774 | 1499.544 | 1515.391 | 1532.594 | 1552.003 | 1568.200 | 1577.506 | 1585.030 |
| 2 | 1411.765 | 1418.486 | 1435.574 | 1455.403 | 1475.662 | 1501.108 | 1516.455 | 1533.138 | 1552.142 | 1568.058 | 1577.218 | 1584.158 |
| 3 | 1415.813 | 1423.042 | 1439.041 | 1458.228 | 1477.807 | 1502.217 | 1517.254 | 1533.682 | 1552.282 | 1567.916 | 1576.930 | 1583.723 |
| 4 | 1420.352 | 1427.156 | 1442.404 | 1461.064 | 1479.832 | 1503.655 | 1518.320 | 1534.363 | 1552.421 | 1567.774 | 1576.642 | 1583.288 |
| 5 | 1424.685 | 1430.937 | 1445.783 | 1464.159 | 1481.990 | 1505.227 | 1519.254 | 1534.909 | 1552.561 | 1567.631 | 1576.211 | 1582.852 |
| 6 | 1429.044 | 1435.216 | 1449.178 | 1467.018 | 1484.154 | 1506.670 | 1520.324 | 1535.454 | 1552.700 | 1567.489 | 1575.923 | 1582.418 |
| 7 | 1433.074 | 1439.400 | 1452.467 | 1469.450 | 1486.004 | 1508.117 | 1521.395 | 1536.000 | 1552.840 | 1567.347 | 1575.492 | 1581.983 |
| 8 | 1437.245 | 1443.006 | 1455.771 | 1472.142 | 1488.180 | 1509.434 | 1522.467 | 1536.820 | 1553.049 | 1567.205 | 1575.205 | 1581.549 |
| 9 | 1441.441 | 1446.630 | 1458.967 | 1474.780 | 1490.041 | 1510.754 | 1523.407 | 1537.367 | 1553.258 | 1567.134 | 1574.774 | 1581.115 |
| 10 | 1445.179 | 1450.029 | 1462.051 | 1477.365 | 1492.164 | 1512.274 | 1524.280 | 1538.051 | 1553.398 | 1567.063 | 1574.631 | 1580.681 |
| 11 | 1448.692 | 1453.689 | 1464.779 | 1479.896 | 1494.228 | 1513.731 | 1525.222 | 1538.736 | 1553.677 | 1566.992 | 1574.488 | 1580.391 |
| 12 | 1452.223 | 1456.630 | 1467.516 | 1482.308 | 1496.298 | 1515.059 | 1526.165 | 1539.421 | 1553.817 | 1566.921 | 1574.344 | 1579.958 |
| 13 | 1455.648 | 1459.953 | 1470.388 | 1484.919 | 1497.725 | 1516.189 | 1527.176 | 1539.970 | 1554.097 | 1566.779 | 1573.914 | 1579.092 |
| 14 | 1458.967 | 1463.043 | 1473.146 | 1486.835 | 1499.935 | 1517.520 | 1527.987 | 1540.656 | 1554.376 | 1566.779 | 1573.914 | 1579.092 |
| 15 | 1462.548 | 1466.707 | 1475.914 | 1489.655 | 1501.499 | 1518.854 | 1528.933 | 1541.343 | 1554.656 | 1566.708 | 1573.627 | 1578.803 |
| 16 | 1465.649 | 1469.388 | 1478.693 | 1491.262 | 1503.197 | 1519.989 | 1529.948 | 1541.894 | 1554.936 | 1566.636 | 1573.484 | 1578.371 |
| 17 | 1469.138 | 1472.769 | 1481.228 | 1493.453 | 1504.768 | 1521.228 | 1530.897 | 1542.582 | 1555.216 | 1566.565 | 1573.341 | 1577.938 |
| 18 | 1472.393 | 1475.662 | 1484.026 | 1495.651 | 1506.473 | 1522.534 | 1531.711 | 1543.133 | 1555.496 | 1566.494 | 1573.054 | 1577.650 |
| 19 | 1475.536 | 1478.566 | 1486.452 | 1498.894 | 1508.182 | 1523.742 | 1532.798 | 1543.546 | 1555.776 | 1566.452 | 1572.911 | 1577.362 |
| 20 | 1478.566 | 1481.609 | 1488.885 | 1500.496 | 1510.028 | 1524.953 | 1533.546 | 1544.236 | 1556.409 | 1566.409 | 1572.625 | 1577.074 |
| 21 | 1481.481 | 1484.409 | 1491.198 | 1502.347 | 1511.877 | 1526.030 | 1534.363 | 1544.788 | 1556.336 | 1566.352 | 1572.339 | 1576.642 |
| 22 | 1484.281 | 1487.091 | 1493.647 | 1504.113 | 1513.334 | 1526.974 | 1535.181 | 1545.341 | 1556.476 | 1566.338 | 1572.195 | 1576.355 |
| 23 | 1487.219 | 1489.912 | 1496.233 | 1505.817 | 1515.191 | 1528.189 | 1536.000 | 1545.894 | 1556.757 | 1566.310 | 1571.909 | 1575.923 |
| 24 | 1489.784 | 1492.357 | 1498.569 | 1507.788 | 1516.654 | 1529.271 | 1536.956 | 1546.586 | 1557.037 | 1566.281 | 1571.766 | 1575.636 |
| 25 | 1492.744 | 1495.068 | 1500.782 | 1509.500 | 1518.253 | 1530.423 | 1537.777 | 1547.139 | 1557.318 | 1566.253 | 1571.624 | 1575.205 |
| 26 | 1495.198 | 1497.400 | 1502.870 | 1511.348 | 1519.722 | 1531.508 | 1538.462 | 1547.694 | 1557.458 | 1566.225 | 1571.338 | 1574.774 |
| 27 | 1497.790 | 1499.606 | 1505.227 | 1513.069 | 1521.328 | 1532.730 | 1539.352 | 1548.248 | 1557.739 | 1566.211 | 1571.052 | 1574.488 |
| 28 | 1500.130 | 1501.956 | 1506.802 | 1515.125 | 1522.668 | 1533.682 | 1540.176 | 1548.803 | 1558.020 | 1566.182 | 1570.909 | 1574.201 |
| 29 | 1502.739 | 1504.178 | 1509.039 | 1516.787 | 1524.146 | 1534.636 | 1541.137 | 1549.359 | 1558.301 | 1566.154 | 1570.766 | 1573.914 |
| 30 | 1505.227 | 1506.408 | 1511.018 | 1518.587 | 1525.626 | 1535.591 | 1541.825 | 1549.776 | 1558.582 | 1566.125 | 1570.624 | 1573.484 |
| 31 | 1507.327 | 1508.643 | 1412.870 | 1519.923 | 1527.109 | 1536.410 | 1542.513 | 1550.332 | 1558.863 | 1566.097 | 1570.481 | 1573.197 |
| 32 | 1509.830 | 1510.622 | 1514.992 | 1521.596 | 1528.324 | 1537.503 | 1543.339 | 1550.749 | 1559.145 | 1566.069 | 1570.195 | 1572.911 |
| 33 | 1511.943 | 1512.473 | 1516.854 | 1523.138 | 1529.677 | 1538.462 | 1544.167 | 1551.117 | 1559.285 | 1566.040 | 1570.053 | 1572.625 |
| 34 | 1513.798 | 1514.328 | 1518.587 | 1524.482 | 1530.626 | 1539.352 | 1544.857 | 1551.864 | 1559.356 | 1566.012 | 1569.767 | 1572.339 |
| 35 | 1516.055 | 1516.322 | 1520.019 | 1525.963 | 1531.983 | 1540.313 | 1545.617 | 1552.282 | 1559.567 | 1565.983 | 1569.625 | 1571.909 |
| 36 | 1517.920 | 1518.187 | 1521.931 | 1527.581 | 1533.274 | 1541.137 | 1546.309 | 1552.700 | 1559.708 | 1565.955 | 1569.482 | 1571.624 |
| 37 | 1519.789 | 1520.090 | 1523.541 | 1528.933 | 1520.500 | 1542.169 | 1547.139 | 1553.258 | 1560.060 | 1565.927 | 1569.340 | 1571.338 |
| 38 | 1521.529 | 1521.797 | 1525.155 | 1530.287 | 1535.454 | 1542.995 | 1547.694 | 1553.677 | 1559.989 | 1565.856 | 1569.055 | 1570.909 |
| 39 | 1523.407 | 1523.541 | 1526.772 | 1531.643 | 1536.683 | 1543.822 | 1548.387 | 1554.097 | 1560.130 | 1565.785 | 1568.912 | 1570.624 |
| 40 | 1525.155 | 1525.424 | 1528.392 | 1532.866 | 1537.778 | 1544.788 | 1549.081 | 1554.516 | 1560.271 | 1565.714 | 1568.628 | 1570.195 |
| 41 | 1526.772 | 1527.041 | 1529.610 | 1533.955 | 1538.599 | 1545.479 | 1549.637 | 1554.936 | 1560.553 | 1565.643 | 1568.485 | 1569.767 |
| 42 | 1528.527 | 1528.527 | 1531.236 | 1535.113 | 1539.695 | 1546.309 | 1550.193 | 1555.216 | 1560.533 | 1565.572 | 1568.343 | 1569.340 |
| 43 | 1529.881 | 1530.016 | 1532.594 | 1536.341 | 1540.656 | 1546.790 | 1550.749 | 1555.636 | 1560.694 | 1565.501 | 1568.058 | 1568.912 |
| 44 | 1531.643 | 1531.643 | 1533.955 | 1537.435 | 1541.618 | 1547.486 | 1551.306 | 1555.916 | 1560.694 | 1565.430 | 1567.774 | 1568.628 |
| 45 | 1553.002 | 1533.138 | 1535.181 | 1538.667 | 1542.375 | 1548.318 | 1551.864 | 1556.336 | 1561.117 | 1565.288 | 1567.489 | 1568.343 |
| 46 | 1534.363 | 1534.363 | 1536.273 | 1539.627 | 1543.408 | 1548.803 | 1552.282 | 1556.617 | 1560.976 | 1565.217 | 1567.347 | 1568.058 |
| 47 | 1535.727 | 1535.591 | 1537.503 | 1540.656 | 1544.236 | 1549.498 | 1552.700 | 1556.897 | 1560.976 | 1565.076 | 1567.063 | 1567.631 |
| 48 | 1536.956 | 1536.683 | 1538.599 | 1541.687 | 1544.857 | 1550.054 | 1553.258 | 1557.178 | 1561.187 | 1564.934 | 1566.921 | 1567.205 |
| 49 | 1538.325 | 1538.051 | 1539.558 | 1542.513 | 1545.686 | 1550.610 | 1553.677 | 1557.458 | 1561.328 | 1564.792 | 1566.636 | 1566.779 |
| 50 | 1539.421 | 1539.147 | 1540.519 | 1543.477 | 1546.378 | 1551.167 | 1554.097 | 1557.739 | 1561.117 | 1564.651 | 1566.352 | 1566.352 |

Sonic Velocities - meters per second

Thus, with the temperature of and sonic velocity in the electrolyte known or measured, the specific gravity of the electrolyte can be determined from the comparison with the database. Because of the matrix nature of the database, the actual value of the third parameter, for example specific gravity, most accurately would be determined by interpolation between the numerical values given in Table I for the two input parameters, for example temperature and sonic velocity.

The disclosed ultrasonic hydrometer 42 can be used on most any conventional lead acid battery where no variation or modification need be made thereto; the only criteria being to find a reliable "sonic path". The "sonic path" must have the spaced sonic surfaces disposed under the level of the electrolyte, the electrolyte must extend continuously between the spaced sonic surfaces, no intervening structure can be disposed between the spaced sonic surfaces, and good sound transmitting contact must be made between the probe head and battery case wall. The sonic paths 30, 32, 34 and 36 have been illustrated of different possible locations and angles that might be used on a battery that has not otherwise been modified. To use the sonic paths 30 or 32, the probe head will be placed against the top wall 20 or against the bottom wall 22. In like manner, to use the sonic path 34, the probe head can be placed against the near side wall 24 or the remote side wall 23; while to use sonic path 36, the probe head can be disposed against the end wall 26. In this regard, the sonic path 36 extends between the end wall 26 and the partition wall 28 between the individual cells 14 and 15.

Once specific "sonic paths" have been found on a conventional battery, the corresponding contact pad areas 40 can be marked at the specific locations on the battery. This would indicate where on the battery the probe head could be placed to have a good sonic path. These modifications to commercially available batteries, although not needed, would be desirable to enhance the appeal and accuracy of this invention.

A battery could be specifically modified to have the pad areas 40 and sonic surfaces designed into the battery, as illustrated with respect to sonic paths 31, 33 and 35. Thus spacer nubs 71, 73 and 75 are formed on the side walls of the battery, protruding beyond the normal contour of the side wall. Each spacer nub is hollow and has a curved side wall 78 and spaced upper and lower sonic surfaces formed on the inside of corresponding upper and lower walls 79 and 80. A cavity defined therebetween is intentionally free of any intervening structure and becomes filled with the battery electrolyte. The upper wall 79 opposite the upper sonic surface has a contact pad area 40 against which the probe head can be placed. The distance between the spaced sonic surfaces of any one sonic path could be accurately known for easy use of the subject apparatus.

With this design, at least one spacer nub (only nubs 71, 73 and 75 being shown) could be formed on each side wall to space the battery a minimum gap from any adjacent structure for providing cooling air circulation around the battery. Specifically, in a three-cell, six-volt battery, the two end cells could have the spacer nubs 71 and 75 located on the opposite end walls, and the interior cell could have a pair of spacer nubs (only nub 73 being shown) formed on the opposite side walls.

Figure 4:
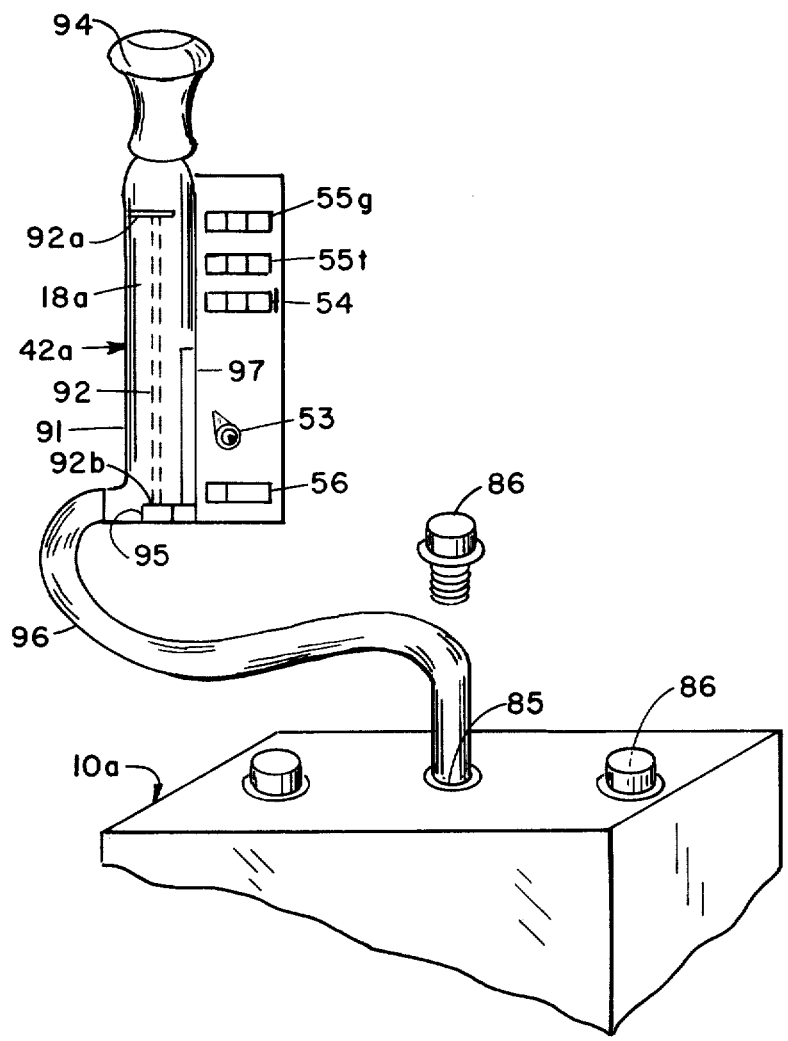
FIG. 4 is a perspective view of an alternate embodiment of the subject ultrasonic hydrometer apparatus shown in operative association with a wet battery having removable water filler caps, where some battery electrolyte is moved from the battery into the apparatus for determining the specific gravity of the electrolyte.

FIG. 4 illustrates a second embodiment of ultrasonic hydrometer apparatus 42a that can be used with any battery 10a having electrolyte filler openings 85 and removable caps 86 for closing the openings. The hydrometer apparatus has a housing 91 with a hollow and liquid-tight chamber 18a having spaced sonic surfaces 92a and 92b that define therebetween sonic path 92. A flexible squeeze bulb 94 closes the top of the hollow chamber. A tube 96 connected to the hollow chamber near its lower end is designed to fit into a battery cell through the filler opening after removing the filler cap 86. An ultrasonic transducer 95 is located in the housing directly against the underside of the lower wall opposite the sonic surface 92a. No intervening structure is located between the sonic surfaces 92a and 92b. Likewise, a thermocouple 97 is located within the housing to sense the temperature of the liquid electrolyte drawn into the chamber. The control for operating the hydrometer will not be described, inasmuch as it is similar to the hydrometer described with respect to FIGS. 1 and 5, and accordingly will have the similar displays 55g and 55t for the specific gravity and temperature thumb wheel input 54, and mode selector and on-off switches 53 and 56, respectively. Since the sonic surfaces are fixed and will be universally used for every test reading, the distance therebetween will be accurately known and can be inputed into the microprocessor, so no distance display need be used.

The ultrasonic hydrometer apparatus 42a illustrated in FIG. 4 could be used on existing batteries having filler caps, free from the possible difficulty in finding a suitable sonic path on the battery. The apparatus 42a would be operated by squeezing and then releasing the bulb 94, to allow the collapsed bulb upon expanding to its original shape to draw the battery electrolyte up into the housing. Activation of the pulser would produce an ultrasonic impulse which would traverse the electrolyte, and the time required to travel through the battery electrolyte back and forth between the sonic surfaces would be measured. The spacing between the sonic surfaces would be accurately known, and the microprocessor would be calibrated accordingly. The ultrasonic hydrometer 42a is thus relatively easy to operate and foolproof in that the operator need not maintain the hydrometer truly vertical when activating the ultrasonic pulse, while further determined specific gravity would be visually indicated and this readout can be retained on the device, if desired, until it were intentionally cancelled out.

It can be noted also that the liquid-air interface at the upper surface of the electrolyte in the battery is sufficient to serve as a "sonic surface" in reflecting a sonic pulse coming upon it through the electrolyte. Thus, the transducer probe 44 can be positioned against a lower battery case wall in order to input the ultrasonic pulse from one real sonic surface into the electrolyte in an upward direction where the overlying electrolyte surface will act then to echo the impulse back toward the transducer for detection and timing.

FIG. 6 depicts in graphic form part of a database relating the sonic velocity through sulfuric acid as a function of different concentrations (specific gravities) and temperatures. The database is given also in Table I. All values for the specific gravity have been corrected to the standard temperature of 25° C. so that all readings at any other temperatures will reflect this automatically. In the application of the subject invention, the sensitivity of the transducer allows velocity resolutions of ±0.25 meters per second; but considering the overall accuracy in the measurement of distances and temperatures, and the response delays of the control this will be reduced to approximately ±2 meters per second. This corresponds to a determination of the specific gravity of ±0.15%.

At the specific gravity (density) of approximately 1.245, no change in velocity occurs over the temperature range of interest, between 0° and 40° C. For specific gravities between approximately 1.05 and 1.30 for temperatures between approximately 0° C. and 40° C., each pair of sonic velocity and temperature values will be associated with only one value of specific gravity. Beyond these ranges, it is possible to have the same sonic velocity for two different values of temperature and/or specific gravity. To eliminate this, the ultrasonic hydrometer should be limited to operation for specific gravities and temperatures only in these approximate ranges.

The use of ultrasonic testing apparatus is straightforward if the distance of the sonic path is known. By shifting the mode selector switch 53 to the specific distance parameter, this "distance" can be inputed with the thumb wheel switch (in centimeters, such as 14.78" cms). Thereafter the activation of the impulse signal automatically triggers the transducer and begins the timer. The returning signal stops the timer, so that the time required for the impulse to travel back and forth between the sonic surfaces is measured. The microprocessor then calculates the sonic velocity. The temperature is inputed with the thermocouple 46. The microprocessor then searches the database, having the sonic velocity and temperature inputs, to determine the specific gravity which is automatically corrected to read at 25° C. If the hydrometer 42 is to be used on the same cell with the same sonic path for sustained testing, it is possible that this distance can be retained in memory in the microprocessor so it need not be inputed each time a reading is to be taken.

In order to use the hydrometer 42 on a battery where the distance between the spaced sonic surfaces of the battery is not accurately known, it is necessary first to find this distance. This is done by using a conventional float hydrometer to find the specific gravity of the battery electrolyte at the given electrolyte temperature and adjusting this to correspond to the value at 25° C. This value is inputed by positioning the mode selector switch 53 to "specific gravity" and dialing the thumb wheel switch 54. Thereafter the ultrasonic hydrometer can be used at the same battery condition to obtain the transit time along some sonic path between the two sonic surfaces and to obtain the temperature of the electrolyte. Inasmuch as the two known parameters of the specific gravity and temperature uniquely will identify the sonic velocity, having the time known will allow the microprocessor to calculate with Eq. 3, on a one time basis, the distance traversed by the sonic pulse, and this parameter would be illustrated on the readout display 55d. Once a particular sonic path distance has been calibrated, the ultrasonic hydrometer apparatus could thereafter be used on the same path by inputing this distance (or be retaining this distance in memory), whereupon the specific gravity could be determined directly.

As the battery charges and discharges, the heavier electrolyte migrates toward the bottom of the battery, leading to stratification of the electrolyte. The ultrasonic method averages localized differences in the density of the electrolyte, since the pulse energy travels through various depth layers or broad lateral stratifications of the electrolyte. This is in contrast to readings obtained with a float hydrometer where only a finite amount of electrolyte is drawn from the battery, usually from the top of the cell, and the differences in densities as between the top and the bottom of the cell will not be sensed. It is more accurate therefore to bubble the cell with the electrolyte withdrawal tube of the hydrometer, or with a bubbler used specifically for this purpose, in order to mix the electrolyte during charge and discharge cycles before taking any readings. The mechanical mixing eliminates the stratification of the electrolyte and allows close correlation of specific gravity readings obtained with the float hydrometer and the ultrasonic hydrometer.

It should be noted that this invention would have particular utility in obtaining at frequent intervals the specific gravity readings on a test battery that would be under cyclic charge and discharge conditions, where each cycle may be completed over a several hour period, and further where the voltage and amperage readings can simultaneously be taken. For such a use, the various readings could be recorded also on a computer for complete data retention and analysis.

The embodiments of the invention in which an exclusive property or privilege is claimed are defined as follows:

1. A portable ultrasonic hydrometer for determining the specific gravity of the electrolyte in a wet battery such as lead-acid battery having a case with one sonic surface formed on the inside of the battery case under the level of the electrolyte and with an opposing sonic surface boundary of the electrolyte spaced a distance "d" therefrom, the combination comprising sensing means for determining the temperature of the electrolyte, transduer means, a probe for holding the temperature sensing and transducer means whereby they can be hand held flush against the outside of the battery case opposite the one sonic surface, means for exciting the transducer means to emit an ultrasonic impulse against the outside of the case for transmssion through the case and from the one sonic surface into the electrolyte, whereby the impulse traverses the electrolyte, reflects off the spaced opposing sonic surface boundary and returns through the electrolyte to and is detected by the transducer means, timer means for measuring the lapsed time "t" between the initial impulse of the transducer means and the detected returning impulse, means for calculating with the equation "$V=2d/t$" the sonic velocity "V" through the electrolyte, means including a database corelating the sonic velocity in and the temperature and specific gravity of the electrolyte for temperature values between 0° and 40° C. and for specific gravity values between 1.05 and 1.30, means for searching the database for specifically known inputs including the calculated sonic velocity in and measured temperature of the electrolyte for determining the corresponding specific gravity of the electrolyte, housing means, and said exciting means, timer means, calculating means and searching means being disposed in the housing, and flexible conductor means between the housing means and the probe.

2. An ultrasonic hydrometer according to claim 1, further providing in the combination that the opposing sonic surface boundary is formed as part of the battery case disposed also under the level of the battery electrolyte, and wherein the electrolyte continuously fills the space between the sonic surfaces along a straight sonic path and to the exclusion of intervening structure.

3. An ultrasonic hydrometer according to claim 1, further including selector mode control means and manually operable input means connected thereto each disposed in the housing, whereby a known value for either of two parameters including the distance "d" between the sonic surfaces and the specific gravity of the electrolyte can be inputed with the input means and selector mode control means into the means including the database, so that with this parameter and the electrolyte temperature parameter known the database then can be searched for the remaining unknown parameter to satisfy uniquely the calcuation of equation "$V=2d/t$".

4. A portable ultrasonic hydrometer for measuring the specific gravity of the electrolyte of a wet battery such as a lead-acid battery having a case filled with the electrolyte and an electrolyte filler opening closed by a removable cap, the combination comprising a housing having a hollow chamber, means for drawing the electrolyte from the battery and through the filler opening to fill the hollow chamber, opposed sonic surfaces located in the chamber, said sonic surfaces being spaced apart by a distance "d" along a straight sonic path to the exclusion of intervening structure and each being under the level of the electrolyte when the latter is filling the chamber, sensing means in the housing for determining the temperature of the electrolyte, transducer means associated with one sonic surface and means for exciting the transducer means for emitting an ultrasonic impulse for transmission through the electrolyte and reflection off the spaced opposing sonic surface so as to return to and be detected by the transducer means, timer means for measuring the lapsed time "t" between the initial impulse and the detected returning impulse, means for calculating with the equation "$V=2d/t$" the sonic velocity "V" through the electrolyte, means including a database correlating the sonic velocity in and the temperature and specific gravity of the electrolyte for temperature values between 0° and 40° C. and for specific gravity values between 1.05 and 1.30, and means for searching the database for specifically known inputs including the calculated sonic velocity in and measured temperature of the electrolyte for determining the corresponding specific gravity of the electrolyte.

5. A method for determining the condition of a wet battery such as a lead-acid battery having a case filled with battery electrolyte, comprising the steps of locating two sonic surfaces spaced apart by a distance "d" and defining therebetween a straight sonic path continuously under the electrolyte and to the exclusion of intervening structure, one of the sonic surfaces being formed on the inside of the battery case and opposite an area on the exterior of the battery case that is exposed and accessible, emitting an ultrasonic impulse against the exposed exterior area of the case for transmission from the one sonic surface and through the electrolyte to reflect off the spaced opposing sonic surface boundary so as to return to the one sonic surface, detecting the returning impulse and measuring the lapsed time "t" between the initial impulse being triggered and the returning impulse being detected, calculating with the equation "$V=2d/t$" the sonic velocity "V" through the electrolyte, measuring the temperature of the electrolyte, and using a database correlating the sonic velocity in and the temperature and specific gravity of the electrolyte for temperature values between 0° and 40° C. and for specific gravity values between 1.05 and 1.30 for specifically known inputs including the calculated sonic velocity in and measured temperature of the electrolyte and obtaining thereby the corresponding specific gravity of the electrolyte.

6. In a wet battery such as a lead-acid battery having a case, current collecting plates in the case, and electrolyte filling the case and covering the plates, the improvement comprising the case being formed of interconnected side walls that transmit ultrasonic impulses, one of said case side walls having a small hollow spacer lug formed thereon, the lug having two walls that are spaced apart and defining on the insides thereof a pair of sonic surfaces, said sonic surfaces being spaced apart by a distance "d" and being substantially parallel to and facing one another and defining a space therebetween to the exclusion of intervening structure, the sonic surfaces each being under the level of the electrolyte and the electrolyte filling the space therebetween continuously so as to define a straight sonic path back and forth between the sonic surfaces that traverse only through the electrolyte, and one of the two lug walls having an exterior contact area opposite one of the sonic surfaces that is exposed and accessible, whereby a transducer can be positioned against the contact area to send an ultrasonic impulse through the case wall and from the one sonic surface through the electrolyte to reflect then off the other sonic surface and be detected at some incremental time "t" later by the transducer, so that the sonic velocity "V" can be calculated with the equation "$V=2d/t$", and whereby this sonic velocity and the electrolyte temperature can be checked against a database correlating the three parameters of sonic velocity in and temperature and specific gravity of the electrolyte so that the unknown specific gravity can be determined.

* * * * *